(12) United States Patent
Berry

(10) Patent No.: US 6,342,053 B1
(45) Date of Patent: Jan. 29, 2002

(54) APPARATUS FOR CORNEA RESHAPING

(75) Inventor: Michael J. Berry, The Woodlands, TX (US)

(73) Assignee: Laser Biotech, Inc., Fremont, CA (US)

( * ) Notice: Subject to any disclaimer, the term of this patent is extended or adjusted under 35 U.S.C. 154(b) by 0 days.

(21) Appl. No.: 08/192,979

(22) Filed: Feb. 8, 1994

Related U.S. Application Data

(60) Division of application No. 07/596,060, filed on Oct. 11, 1990, now abandoned, which is a continuation-in-part of application No. 07/556,886, filed on Jul. 23, 1990, now abandoned.

(51) Int. Cl.$^7$ .............................................. A61F 9/013
(52) U.S. Cl. ................. 606/5; 606/3; 606/10; 606/13; 606/27
(58) Field of Search .............................. 606/2, 3, 4–18, 606/27

(56) References Cited

U.S. PATENT DOCUMENTS

| | | |
|---|---|---|
| 3,776,230 A | 12/1973 | Neefe |
| 3,831,604 A | 8/1974 | Neefe |
| 3,982,201 A | 9/1976 | Rosenkrantz |
| 4,330,763 A | 5/1982 | Esterowitz |
| 4,381,007 A | 4/1983 | Doss |

(List continued on next page.)

FOREIGN PATENT DOCUMENTS

| | | |
|---|---|---|
| DE | 3612287 | 10/1987 |
| EP | 214712 | 3/1987 |
| EP | 0249329 A3 | 12/1987 |
| EP | 0395196 A1 | 10/1990 |
| WO | WO8906519 | 7/1989 |
| WO | WO9012618 | 11/1990 |

OTHER PUBLICATIONS

*Ophthalmology Times,* vol. 13, No. 18; used Sep. 15, 1988; L. Bruck, "Soviet Laser is used to correct Hyperopia" see p. 1 and 37.
Advanced Techniques in Ophthalmic Microsyrgery, vol. II Corneal Surgery Nov. 19, 1980 (C.V. Mosby Company), Louis Girard pp. 147–150.
"Thermokeratoplasty in the Treatment of Keratoconus," Gassett et al., Feb. 1985, *American Journal of Ophthalmology.*
"An Electrothermal Technique for the Alteration of Corneal Curvature," Dos et al., Feb. 1978, Los Alamos Scientific Laboratory.
"Los Alamos Keratoplasty Techniques," Rowsey et al., Mar. 1980, *Contact & Intraocular Lens Medical Journal.*

(List continued on next page.)

*Primary Examiner*—David M. Shay
(74) *Attorney, Agent, or Firm*—Skjerven Morrill MacPherson LLP; K. Alison de Runtz

(57) ABSTRACT

An apparatus is described for use in combination with a noninvasive ophthalmological method for cornea reshaping in order to correct ocular refractive errors such as myopia (nearsightedness), hyperopia (farsightedness), and astigmatism. This apparatus is called a coupler and it is made of a material which is substantially transparent to the light energy used to reshape the cornea. The coupler conducts heat from the anterior portion of the cornea during the heating of the stroma by the light energy. The reshaping is enhanced by the coupler as it has a corneal engaging surface with a radius of curvature which approximates the desired emmetropic shape of the cornea. In addition to being a heat sink and template for the eye, the coupler also acts as a positioner and restrainer of the eye by attaching itself to the eye via an annular suction ring. Finally, the coupler also acts as a mask to prevent accidental exposure of the central optic zone to any light energy during the cornea reshaping procedure.

17 Claims, 6 Drawing Sheets

U.S. PATENT DOCUMENTS

| | | |
|---|---|---|
| 4,391,275 A | 7/1983 | Fankhauser |
| 4,461,294 A | 7/1984 | Baron |
| 4,506,962 A | 3/1985 | Roussel |
| 4,526,171 A | 7/1985 | Schachar |
| 4,538,608 A | 9/1985 | L'Esperance, Jr. |
| 4,558,698 A | 12/1985 | O'Dell |
| 4,565,198 A | 1/1986 | Koeniger |
| 4,575,205 A | 3/1986 | Rappazzo |
| 4,580,559 A | 4/1986 | L'Esperance |
| 4,662,370 A | 5/1987 | Hoffmann et al. |
| 4,664,490 A | 5/1987 | Rol |
| 4,665,913 A * | 5/1987 | S'Esperance, Jr. .............. 606/5 |
| 4,712,543 A | 12/1987 | Baron |
| 4,729,373 A | 3/1988 | L'Esperance, Jr. |
| 4,750,829 A | 6/1988 | Wise |
| 4,787,732 A | 11/1988 | Siviglia |
| 4,798,204 A | 1/1989 | L'Esperance, Jr. |
| 4,840,175 A | 6/1989 | Peyman |
| 4,880,001 A | 11/1989 | Weinberg |
| 4,881,543 A | 11/1989 | Trembly |
| 4,903,695 A | 2/1990 | Warner |
| 4,905,711 A | 3/1990 | Bennett |
| 4,907,586 A | 3/1990 | Bille |
| 4,907,872 A | 3/1990 | Schirmer et al. |
| 4,913,142 A | 4/1990 | Kittrell et al. |
| 4,966,452 A | 10/1990 | Shields et al. |
| 4,976,709 A * | 12/1990 | Sand .............................. 606/5 |
| 5,007,729 A | 4/1991 | Erickson et al. |
| 5,009,660 A | 4/1991 | Clapham |
| 5,011,498 A | 4/1991 | Krumeich et al. |
| 5,108,412 A | 4/1992 | Krumeich et al. |
| 5,133,708 A | 7/1992 | Smith |

OTHER PUBLICATIONS

"Ophthalmic Applications of Infrared Lasers—Thermal Considerations," Mainster, Apr. 1989, *Investigative Ophthalmology & Visual Science*.

Spears et al., "Corneal Refractive Correction By Laser Thermal Keratoplasty, Laser–Tissue Interaction," *SPIE,* vol. 1202, p. 334 (1990).

"An Ophthalmic Excimer Laser For Corneal Surgery," Schroeder et al., *Am. J. Ophthal.,* Mar. 1987, vol. 103, No. 3, Part II, pp. 472–473.

* cited by examiner

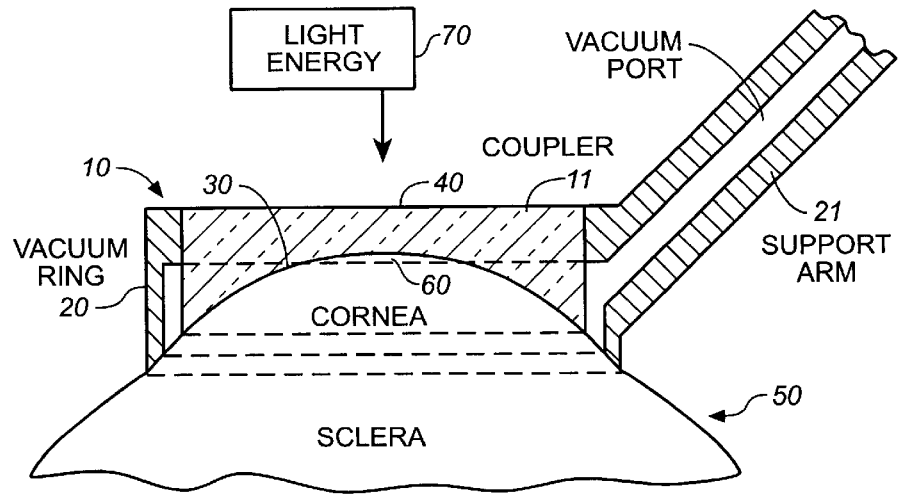
FIG._1
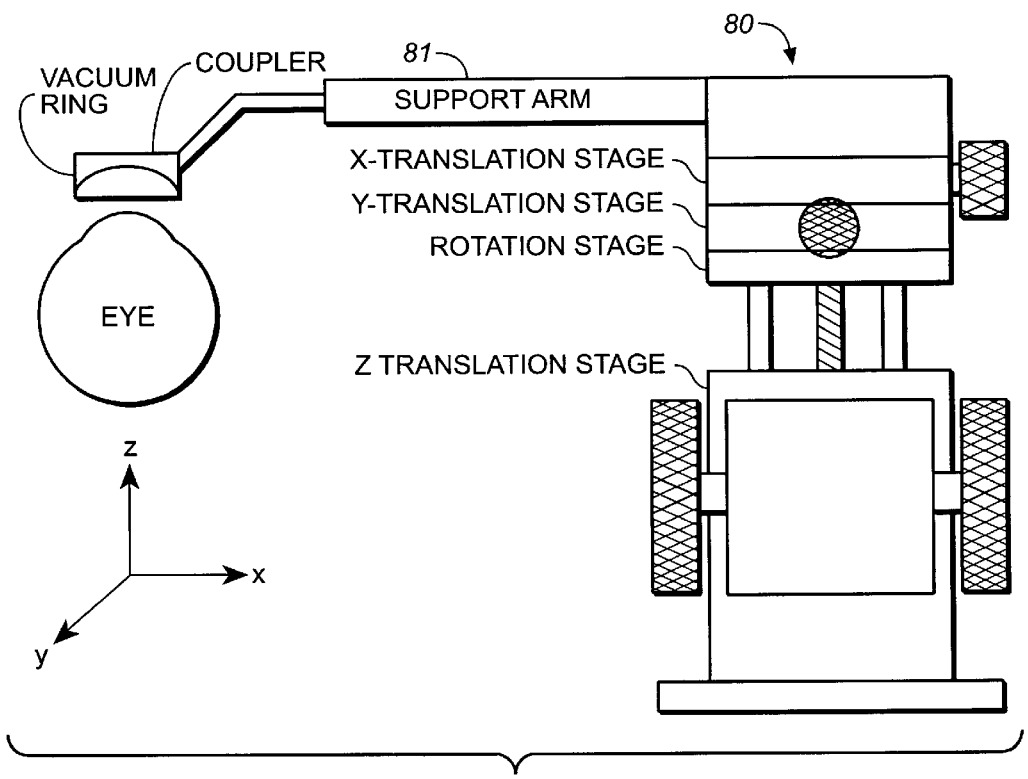
FIG._2

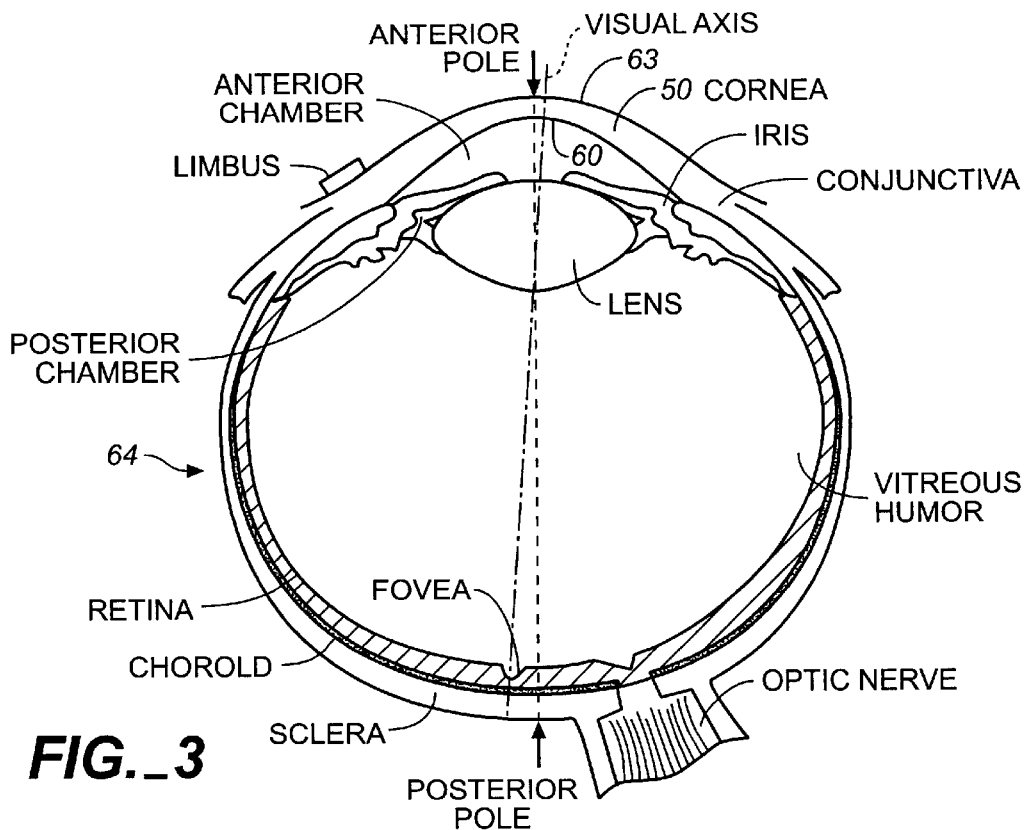
FIG._3
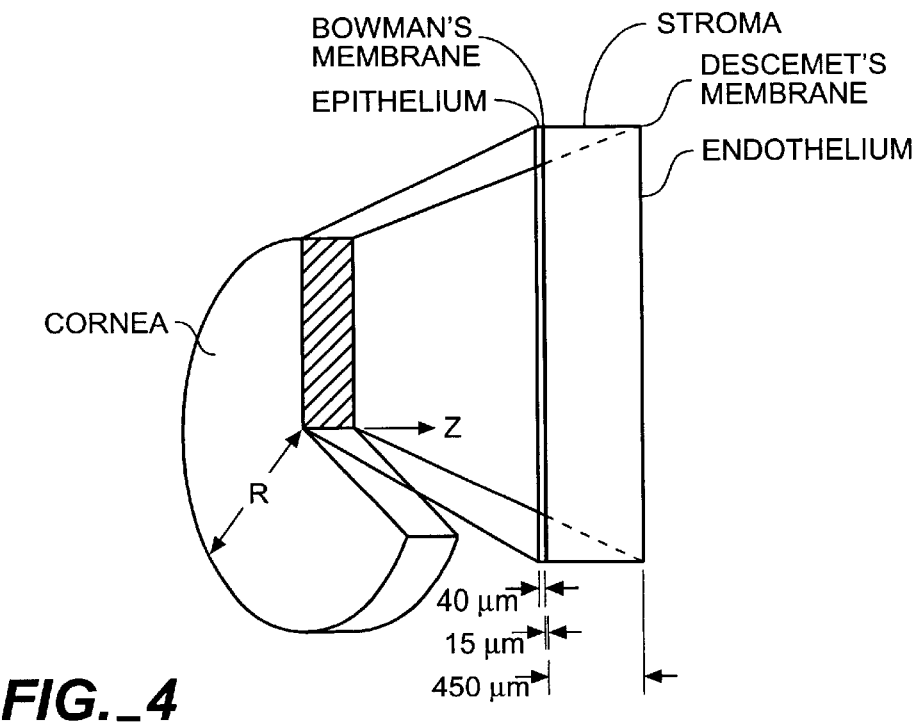
FIG._4

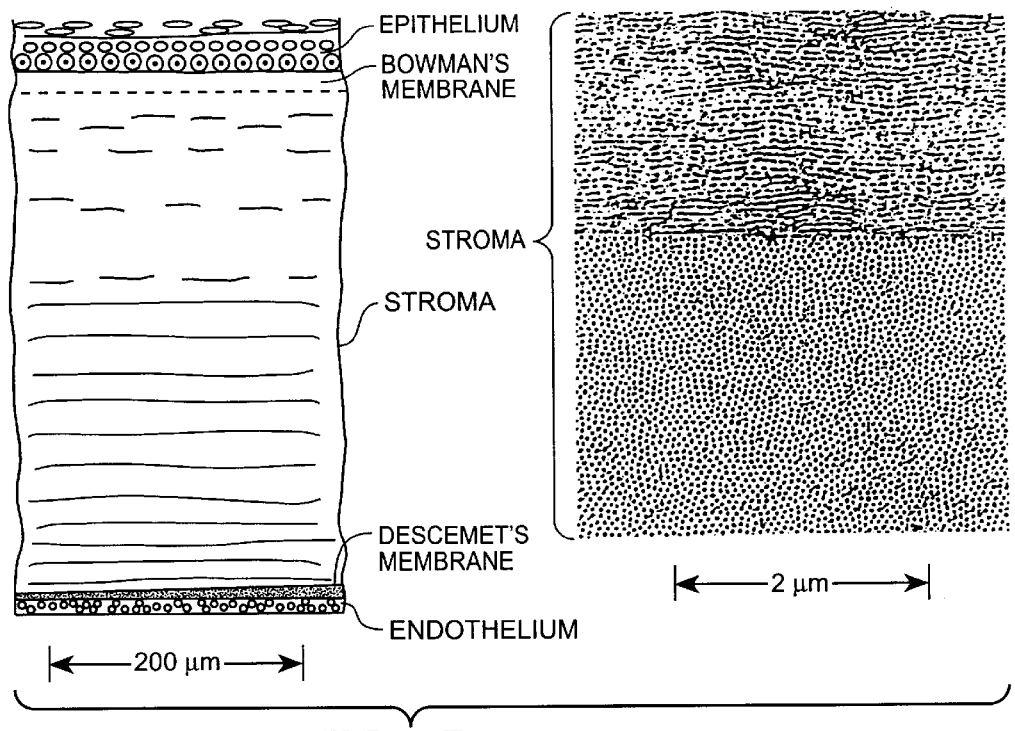
FIG._5
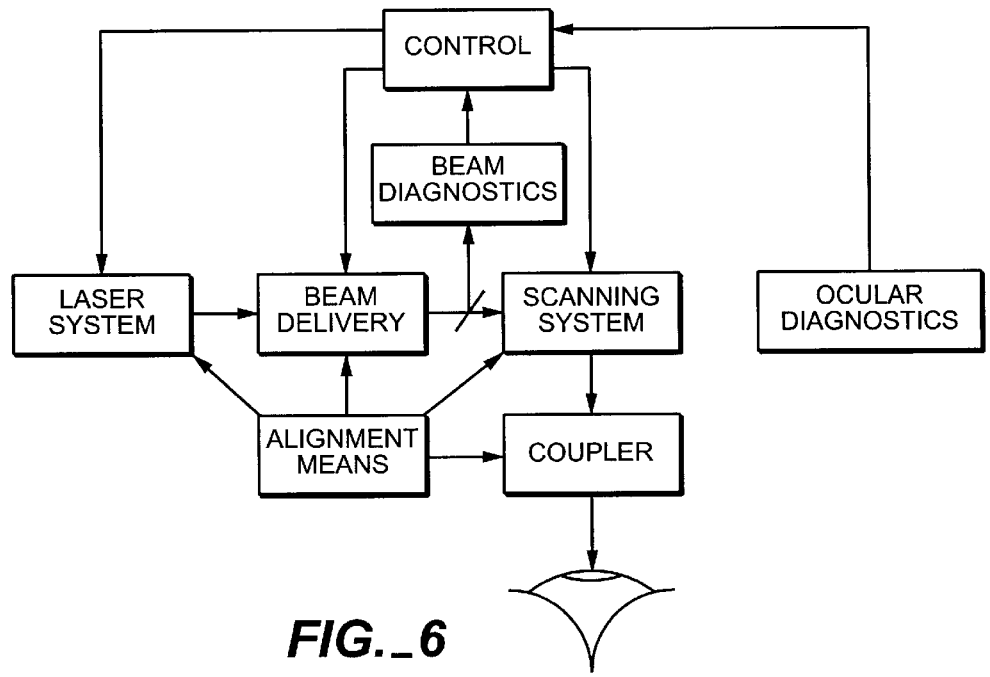
FIG._6

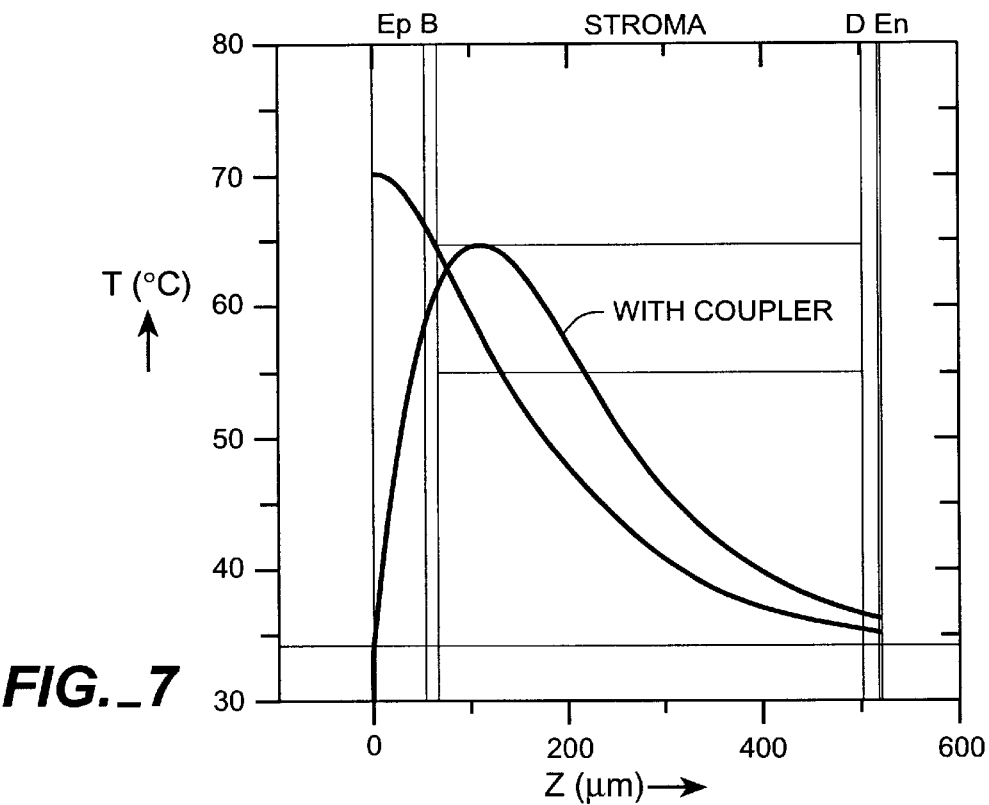
FIG._7
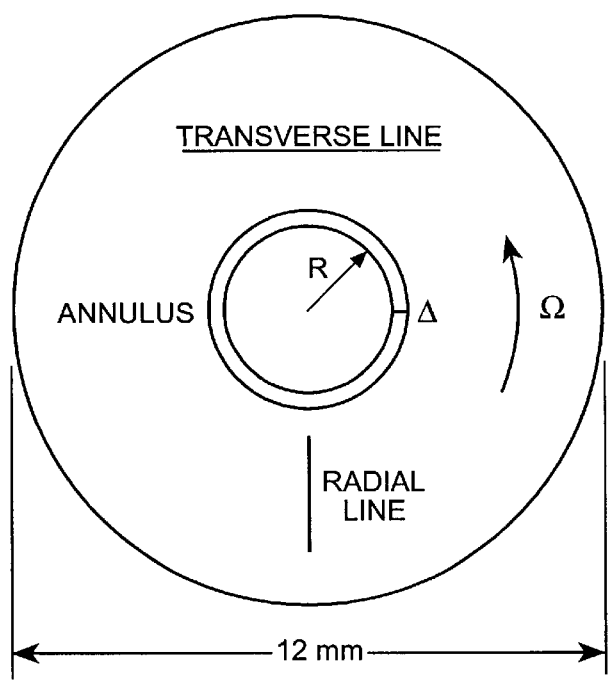
FIG._8

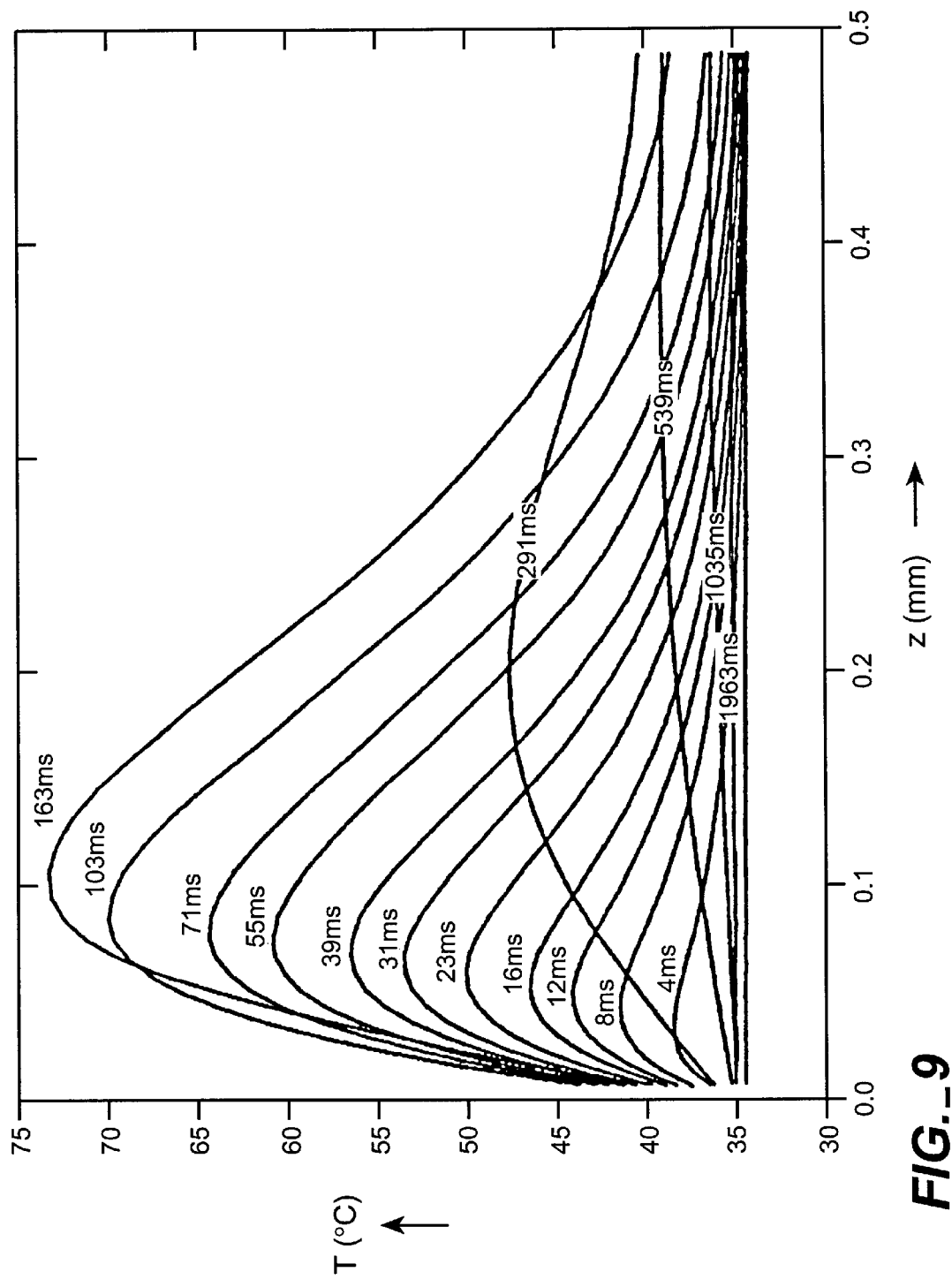
FIG._9

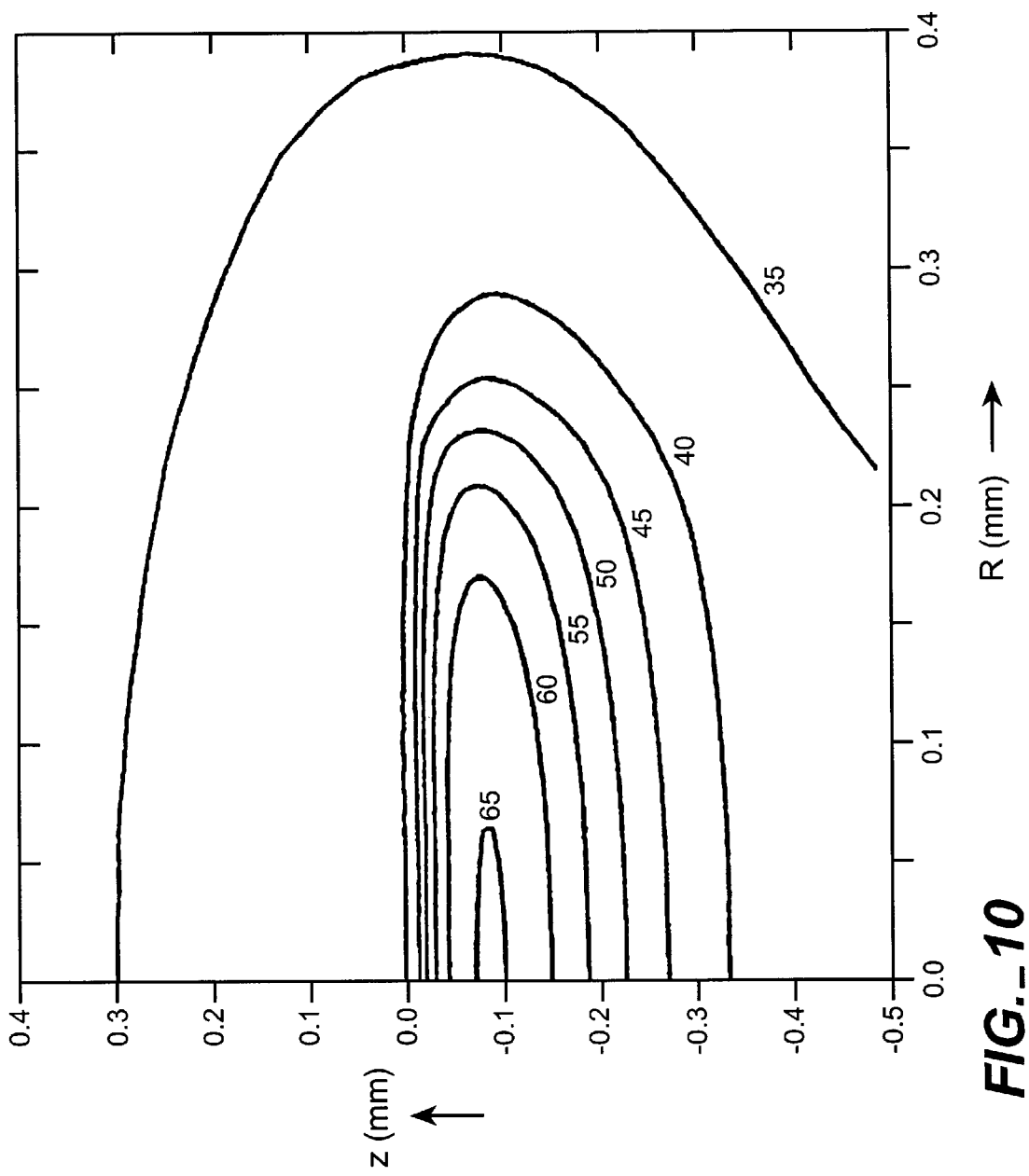
FIG._10

APPARATUS FOR CORNEA RESHAPING

This is a division of application Ser. No. 07/596,060, filed Oct. 11, 1990, now abandoned, which in turn is a continuation-in-part of application Ser. No. 07/556,886, filed Jul. 23, 1990, now abandoned.

BACKGROUND OF THE INVENTION

This invention relates to a coupler apparatus for use in combination with a noninvasive ophthalmological method for reshaping the anterior surface of the cornea in order to achieve emmetropia (i.e., normal vision characterized by the absence of ocular refractive error; the emmetropic eye focuses parallel rays of light onto the retina to produce a clear image). The method of the invention uses light energy to induce thermal changes to the collagen in the stromal portion of the cornea in order to physically reorganize the stromal collagen to produce the desired reshaping of the cornea. The method is described in commonly-assigned, copending U.S. patent application Ser. No. 556,886 filed Jul. 23, 1990 which is hereby incorporated by reference as if fully set forth herein.

The apparatus of this invention is referred to as a coupler based on its utility, which is to couple a heat and light energy source to the cornea surface. It is made of a material which is substantially transparent to the light energy used to reshape the cornea. In this fashion the coupler acts as a heat sink. The coupler conducts heat from the anterior portion of the cornea during the heating of the stroma. The coupler has a corneal engaging surface so that the coupler is positioned on the anterior surface of the cornea. This corneal engaging surface has a radius of curvature which approximates the desired emmetropic shape of the cornea following the heating of the stroma and rearrangement of the collagen.

Today there are over 100 million people in the United States alone who wear eyeglasses or contact lenses to correct ocular refractive errors. The most common ocular refractive errors include myopia (nearsightedness), hyperopia (farsightedness), and astigmatism. In myopia, the refractive power of the eye is excessive meaning that parallel rays of light are focused in front of the retina producing a blurred image. Myopic vision can be modified, reduced or corrected by adding a spherical concave lens of the correct spherical curvature in front of the eye or by flattening the cornea axisymmetrically around the visual axis to reduce its refractive power.

In hyperopia (also termed hypermetropia), the refractive power of the eye is deficient meaning that parallel rays of light are focused behind the retina producing a blurred image. Hyperopic vision can be modified, reduced or corrected by adding a spherical convex lens of the correct spherical curvature in front of the eye or by steepening the cornea axisymmetrically around the visual axis to increase its refractive power.

In astigmatism, the refractive power of the eye is unequal in all meridians meaning that parallel rays of light are focused differently along different meridians producing a blurred image. Astigmatic vision can be modified, reduced or corrected by adding a non-spherical lens of the correct cylindrical curvatures along various meridians in front of the eye or by flattening and/or steepening the cornea with the correct cylindrical curvatures to compensate for refractive errors along various meridians.

Current widely used devices or methods for correcting ocular refractive errors include eyeglasses, contact lenses and refractive surgery such as radial keratotomy. Eyeglasses and contact lenses may be inconvenient, difficult to wear or impediments in daily activities.

Refractive surgery procedures offer an alternative to eyeglasses and contact lenses but these procedures may be difficult to control in order to achieve accurate refractive corrections. Radial keratotomy is a refractive surgical procedure designed to correct myopia. This technique involves making a series of deep, radial incisions in the cornea with a pattern that resembles the spokes of a bicycle wheel. The incisions themselves do not cross the center of the cornea, the central optic zone. The series of symmetrical cuts flatten the cornea.

Significant percentages of patients who have been subjected to radial keratotomy experience overcorrection, undercorrection or induced astigmatism. Radial keratotomy patients may also suffer from side effects and postoperative complications such as fluctuating refraction, glare, reduced night vision, photophobia, endothelial cell loss, and corneal infection. Another postoperative complication of radial keratotomy is permanent weakening of the cornea due to the fact that the technique requires deep incisions that heal quite slowly. Trauma to the eyes may result in the rupture of the incisions leading to catastrophic loss of the cornea in some cases.

Another method of refractive surgery is laser keratomileusis (i.e., carving the cornea by application of laser energy) also termed laser refractive keratectomy or photorefractive keratectomy. This method of refractive surgery is currently being used in clinical trials in man to correct refractive errors. This technique employs the use of a laser that emits ultraviolet light, typically an argon fluoride excimer laser that operates at a wavelength of 193 nanometers. The laser light causes a breakdown of intramolecular bonds resulting in ablation of tissue by photodecomposition. The shape of the cornea is changed by selectively ablating material in the cornea thus "carving" the anterior corneal surface into a new shape. U.S. Pat. No. 4,665,913 discloses one technique of photorefractive keratectomy.

As is the case for other forms of refractive surgery, photorefractive keratectomy may lead to inadequate refractive corrections and to undesirable side effects. Particularly troublesome is the postoperative complication associated with corneal wound repair, a process that tends to "fill in" the ablated cornea volume with a combination of epithelial and stromal tissues. This process in the human cornea is sometimes referred to as a wound-healing response. There are also concerns about the potential phototoxic effect of ultraviolet light generated by corneal tissue fluorescence and the potential toxic effect of molecular ablation products present in the photoablation plume.

Another method of refractive surgery is intrastromal photorefractive keratoplasty. In this technique a laser beam is focussed inside the corneal stromal tissue to modify tissue either by photoablation or by a change in the tissue's viscoelastic properties. U.S. Pat. No. 4,907,586 discloses one such method for optical laser surgery. It is not clear when the supporting work for this patent was performed. The wavelengths of the laser beams to be used are specified to be 526 nanometers, 1.053 microns, or 2.94 microns. Some of these wavelengths (526 nanometers and 1.053 microns) are transmitted, at least in part, through the cornea possibly causing damage to the retina. If laser induced optical breakdown (i.e., laser induced plasma formation) is used to increase the absorption of these wavelengths, the hot plasma will reradiate light with a broad wavelength distribution that includes phototoxic light in the ultraviolet spectral region.

The final wavelength (2.94 microns) specified in U.S. Pat. No. 4,907,586 is absorbed completely in the anterior portion (particularly, the epithelium) of the cornea [G. L. Valderrama, et al., *SPTE Proceedings*, Vol. 1064, 135–145 (1989)] so that it cannot produce intrastromal tissue modification. The alleged intrastromal photorefractive keratoplasty method is unworkable at some wavelengths and undesirable at other wavelengths because there may be severe damage caused to ocular structures.

Thermokeratoplasty is another method that has been used to reshape the cornea. This is done by the application of heat to the cornea. Corneal stromal collagen shrinks when heated to a temperature of 55° to 58° C., without the destruction of the tissue. The stroma is the central, thickest layer of the cornea and consists mainly of collagen fibers. If the pattern of shrinkage is properly selected the resulting change in the stress field and mechanical properties caused by the shrunken collagen fibers can be used to reshape the cornea.

The original thermokeratoplasty technique used was the application of a heated probe to the cornea leading to conductive heating of the stroma. However, the direct application of a heated probe is uncontrolled and unavoidably destructive. This technique caused thermal destruction of the epithelium as well as Bowman's membrane, the important tissue layer immediately underlying the epithelium. Some patients treated with this technique also showed damage to the deeper corneal stroma and endothelium. Additionally, this technique often involved inadequate refractive correction. Others have attempted the correction of hyperopia by using heated needles to burn a series of craters into the cornea. Recently the hot needles have been replaced with a laser in an effort to produce a more controlled thermal deposition. Severe damage to the corneal tissue still occurs and makes these procedures too undesirable for most ophthalmologists to recommend to their patients.

Another method of themokeratoplasty involves microwave heating of the corneal stromal collagen. Microwave energy can be deposited deeply within the corneal stroma. U.S. Pat. No. 4,881,543 discloses one method and apparatus for heating the central stroma of the cornea with microwave electromagnetic energy to the shrinking temperature of the collagen while circulating a cool fluid over the anterior surface of the cornea. However, microwave thermokeratoplasty procedures do not provide the spatial and temporal resolution and control required to perform accurate cornea reshaping without excessive thermal damage to cornea structures.

There is still a need for a method of reshaping the cornea that is safe, effective, and dependable. The apparatus of this invention, used in combination with a method employing light energy to safely reshape the cornea by controlled heating of the stromal collagen, offers a significant advancement to the field of cornea reshaping.

SUMMARY OF THE INVENTION

This invention relates to an apparatus for reshaping the curvature of the cornea of the human eye. The reshaping is intended to correct ocular refractive errors. The means for reshaping is by a controlled heating of the anterior portion of the stroma of the eye. The apparatus of this invention is a coupler which is typically made from infrasil quartz, calcium fluoride, sapphire, diamond or combinations thereof and which is configured to be removably attached to the anterior most surface of the cornea.

The coupler device is highly transparent to the preferred wavelengths of functionally effective light energy. The light energy is typically supplied in the range of 2.4 to 2.67 microns for a hydrogen fluoride chemical laser or 1.90 to 2.02 microns for a thulium doped laser. The function of the coupler is to act as a heat sink and thermostat; a template for the cornea; a positioner and restrainer for the eye; and a mask during the reshaping procedure.

The coupler device has a corneal engaging surface which is functionally sized to be removably attached to the anterior surface of the cornea. In the most preferred embodiment, the corneal engaging surface has the desired emmetropic shape for corrected vision. The radius of curvature of the cornea must be calculated so that a similar curvature of the corneal engaging surface of the coupler device can be used.

The coupler device of this invention also includes means for retaining the coupler on the corneal surface during the treatment procedure. The coupler device further includes means for immobilizing the eye to ensure that the treatment procedure avoids the central optic zone of the eye. The most preferred retaining means and immobilizing means is an annular suction ring.

The coupler device of this invention also functions as a mask to provide a specific pattern of light energy application to the cornea. The specific geometry of the pattern of the masking feature of the coupling device is important to the functioning of the corrective method. In this fashion different corrections and different degrees of correction can be encompassed within a single coupler device with interchangeable or interusable masking means. The masking means is typically found on the surface of the coupler opposite the corneal engaging surface although any of the other surfaces may be functionally effective for masking purposes.

It is important to note that the corneal correction takes place without initiating a wound-healing response. The initiation of a wound-healing response introduces significant error into the treatment and must be avoided. The coupler device of this invention facilitates the protection of the stromal collagen from temperatures and conditions sufficient to initiate such a wound healing response through its various functional capabilities.

Although in the preferred embodiment of this invention a laser light is used in combination with the coupler, other known means for transmitting light energy can also be used. For instance, a fiber optic material can be used to control the light source as well as other light controlling means that are well known to those of ordinary skill in the art.

In the preferred embodiment of this invention, a corneal topography measuring device is used to determine the change in the shape of the cornea of the eye, such devices include a surgical keratometer or photo keratoscope. Likewise, in the preferred embodiment, means are provided for viewing the cornea of the patient's eye, i.e. a surgical microscope, and a refraction measurement system is used to determine the total refraction of all components of the eye. In supplying light energy it is important to observe criteria of pattern application, irradiance levels, duration of application, and wave form. At all times the central optic zone of the eye is protected or shielded from radiation. The avoidance of the central optic zone permits avoidance of the risk of undesirable, long term, adverse effects on sight.

The coupler acts as a heat sink and thermostat by conducting heat away from the anterior portions of the cornea during the heating of the stroma. It is important that the section of the cornea referred to as Bowman's membrane be kept below the stromal collagen shrinkage temperature to avoid damage to Bowman's membrane during the procedure. Bowman's membrane controls the regeneration of the epithelium layer of the cornea, thus the importance of not damaging the membrane with the light energy used to heat the stroma.

The coupler acts as a template for the cornea by having a corneal engaging surface positioned on the anterior surface of the cornea. The corneal engaging surface has a radius of curvature which approximates the desired emmetropic shape of the anterior of the cornea. During the heating process, the cornea is reshaped, and the shape contours to the corneal engaging surface which is the desired emmetropic shape.

The coupler also acts as a positioner and restrainer for the eye by attaching to the eye via attachment means, i.e., an annular suction ring. This attachment allows the optical surgeon to position the eye as desired and also permits holding the eye in a fixed position during the procedure. A vacuum of approximately 10 mm Hg is used to attach the coupler to the eye. In the preferred embodiment of this invention the coupler is attached to a stable platform to insure proper alignment of the light source, coupler and eye at the time of irradiance. In the most preferred embodiment of this invention the stable platform is an articulated arm.

And finally, the coupler acts as a mask to prevent accidental exposure of the central optic zone to any light energy during the irradiance procedure. The masking feature likewise permits selection and control of the geometric pattern for application of light energy. Such control permits specific procedures to be defined and used for specific optical corrections.

BRIEF DESCRIPTION OF THE DRAWINGS

FIG. 1 is a schematic cross sectional view of the coupler device of this invention.

FIG. 2 is a schematic assembly of the platform, articulated arm, coupler device and related equipment used to perform the cornea reshaping procedure.

FIG. 3 is a schematic cross section of the human eye showing several ocular structures.

FIG. 4 is a schematic cross sectional view of the cornea showing dimensions of cornea layers.

FIG. 5 is a schematic representation of cornea microstructure showing important cornea structures.

FIG. 6 is a schematic diagram of the essential components of the apparatus used to perform cornea reshaping to correct refractive errors.

FIG. 7 shows the results of one-dimensional (1D) thermal modeling calculations of temperature distributions as a function of depth of penetration into corneal tissue.

FIG. 8 is a schematic representation of different patterns of treatment on the anterior surface of the cornea. The annulus has a radius R and a width Δ and is drawn using a laser spot that is slewed at an angular velocity Ω.

FIG. 9 shows temperature profiles (T) as a function of depth of penetration into corneal tissue (Z) and as a function of time of exposure to the light energy. The temperature profiles are for points along the centerline (radius=0) of the eye.

FIG. 10 shows isothermal contours as a function of depth of penetration into corneal tissue (Z) and as a function of radial locations around the cornea (R). The isothermal contours are for an exposure time of 80 ms (t=80 ms).

DETAILED DESCRIPTION OF THE INVENTION

Referring now specifically to FIG. 1, the coupler device is shown in schematic cross section. The primary components of the coupling device 10 are transparent body 11, suction ring 20, corneal engaging surface 30 and masking means 40. The cornea itself is identified by the number 50 and the central optic portion of the cornea by the number 60.

It is an important aspect of this invention that the central optic portion 60 of the cornea 50 is not impacted by the light energy 70 which is emitted from an appropriate energy source, i.e. a hydrogen fluoride or thulium doped laser. By avoiding damage to the central optic zone the possibility of long-term, irreversible damage to vision is avoided. The avoidance or minimizing of risk in the treatment process used in conjunction with the coupler of this invention is an important technical and commercial feature.

The corneal engaging surface 30 of the coupler 10 acts to interface between the coupler device 10 and the cornea 50. The coupler device 10 is maintained in position by suction ring 20 which is sized to encompass a substantial portion of the human cornea. It is anticipated that a film of tears or ophthalmic solution may be found between the coupler device 10 and cornea 50. The coupler device 10 is removably attached to the anterior surface of the cornea.

As described hereinabove, the main body of the coupler 10 is made from a transparent material such as infrasil quartz, calcium fluoride, sapphire, diamond or combinations thereof. Other materials that satisfy the functional characteristics of providing a heat sink, template, thermostat, positioner, restrainer and mask can likewise be used. The coupler is used by grasping the suction ring 20 on its outermost edges 21 and pressing the device onto the corneal surface. In this fashion the suction ring acts as both a means for restraining movement of the eye and a means for immobilizing the eye. In the preferred embodiment the coupler 10 is removably mounted in a stable platform 80 (see FIG. 2) to insure that the eye, coupler and light source are maintained in coaxial alignment for the duration of irradiance. In the most preferred embodiment the stable platform includes an articulated arm 81.

In FIG. 2 a schematic representation of the stage assembly 80 with the coupler 10 in place over the eye 50 is shown. An operator has access to the means for determining the change of shape of the cornea of the eye, in the preferred embodiment a surgical keratometer, and also to the means for viewing the cornea 50 of the patient's eye, in the preferred embodiment an ophthalmic surgical microscope. Connections are conveniently made between the surgical microscope, surgical keratometer and beam delivery system (also referred to as light energy) 70 by fiber optic cable. A control panel is actuated and used by the operator to control a display so that appropriate surgical modification can be made to the eye.

Turning next to FIG. 3, the basic components of the human cornea are schematically presented. The cornea 50 is shown without the coupler device 10. The coupler device 10 is specifically sized to be fittably received by the anterior most surface 63 of the cornea.

This invention is an apparatus for use in combination with a noninvasive ophthalmological method for reshaping the anterior surface of the cornea in order to achieve emmetropia (normal vision). The coupler 10 is positioned over the eye 64 during the reshaping procedure. The coupler 10 is made of a material that is substantially transparent to the light energy being used to reshape the cornea 50. The functions of the coupler 10 include acting as: (1) a heat sink and thermostat; (2) a template for the cornea; (3) a positioner and restrainer for the eye; and (4) a mask during the reshaping procedure.

The coupler 10 consists of two major functional parts. The first part is an annular suction ring 20 shown in FIG. 1. The purpose of the annular suction ring 20 is to attach the coupler to the eye by use of a vacuum. A vacuum of approximately 10 mm Hg is used. The functions of positioning and restraining the eye 64 are accomplished by attaching the coupler 10 to the eye 64. These functions are achieved because the coupler 10 can be positioned and maintained in place during the procedure; therefore by being attached to the eye 64, the eye 64 will also be positioned and restrained.

The second major functional part of the coupler 10 is the substantially transparent center portion 11 that has a radially curved surface 30 which approximates the desired emmetropic shape of the anterior portion of the cornea. See FIG. 1. This part of the coupler performs the functions of acting as a heat sink and thermostat, a template for the cornea, and a mask during the reshaping procedure.

The center portion of the coupler may be made of infrasil quartz, calcium fluoride, sapphire, diamond or other material that is substantially transparent and yet rigid enough to act as a template for the cornea and still maintain acceptable heat transfer properties. In the preferred embodiment the coupler is substantially transparent to the higher wavelengths of light emitted from the eye during the modification procedure.

The heat sink and thermostat function is needed to maintain Bowman's membrane at a sufficiently cool temperature to prevent clinically significant damage to this important cell layer. Bowman's membrane controls the regeneration of cells in the epithelial layer of the cornea. It must be protected during the heating of the stroma.

The template for the cornea function is preformed by the corneal engaging surface 30 of the coupler 10. See FIG. 1. The corneal engaging surface 63 of the coupler 10 has a radius of curvature which approximates the desired emmetropic shape of the cornea to be formed by the reshaping procedure. The corneal engaging surface 63 actually rides on a thin tear film or ophthalmic solutions over the surface of the cornea. A thin ophthalmic solution film can be used in conjunction with the coupler to prevent damage to the epithelium or Bowman's membrane if the epithelium has been chemically or surgically removed.

The masking function of the coupler is performed by blocking all light energy from impacting on the central optic zone of the eye. This prevents inadvertent reshaping of the central optic zone of the cornea.

The are several embodiments of the reshaping procedure that may be used. The coupler is used in each embodiment. The variations on the reshaping procedure include: (1) attaching the coupler 10 to the epithelium layer of the cornea and heating the stroma with a single light energy beam; (2) removing the epithelium layer and attaching the coupler 10 to Bowman's membrane and heating the stroma with a single light energy beam; (3) attaching the coupler 10 to the epithelium layer and using multiple light energy beams to heat the stroma; (4) attaching the coupler 10 to Bowman's membrane and using multiple light energy beams to heat the stroma; (5) attaching the coupler 10 to the epithelium layer of the cornea 50 and using an intermittent light energy beam to heat the stroma; and (6) attaching the coupler 10 to Bowman's membrane and using an intermittent light energy beam to heat the stroma. See FIGS. 4 and 5.

The reshaping procedure uses a light source 70 emitting a wavelength or wavelengths with correct optical penetration depths to induce thermal changes in the corneal stromal collagen without damaging the viability of the corneal endothelium or the anterior surface of the corneal tissue and without causing a sufficient wound-healing response to lead to long-term corneal reshaping. The light source is coupled with a light delivery and control means for producing the required radiant exposure time and geometric pattern in order to achieve the desired change in the shape of the cornea. Anterior corneal surface cooling by the coupler is used to prevent damage to the endothelium and to Bowman's layer. Although the reshaping procedure is described herein as being performed only one time, repeated applications of the reshaping procedure may be desirable or necessary and are included within the scope of the invention.

The curvature of the cornea 50 in part controls the refraction of the light received by the lens of the eye 64. Ocular refractive errors of the eye can be corrected by changing the shape of the cornea 50. FIG. 3 identifies the various portions of the human eye 64 schematically. As is apparent from the representation of the human eye in FIG. 3, only a small portion of the cornea is used for actual vision. This portion of the cornea is typically referred to as the central optic zone 60 or central visual zone. The typical central optic zone 60 is 4 millimeters in diameter. Referring now to FIGS. 4 and 5, a cross-section of the cornea 50 is shown together with its various layers. As represented schematically, the epithelium is several layers thick and approximately 40 microns in depth, Bowman's membrane is thinner, approximately 15 microns thick, and the stroma layer is the thickest structure, typically about 450 microns thick. For purposes of this application the anterior portion of the stroma is the anterior 1/3 of the stroma or approximately the first 150 microns of the stromal tissue.

The stroma is composed of various internal layers with the arrangement of the layers being the least organized in the anterior section of the stroma. For purposes of this application, corneal tissue shall refer to the entire corneal structure as shown in FIGS. 3 and 5. The organic matter within the corneal stroma is primarily made up of Type I collagen. The Type I collagen of the cornea, before heat treatment, is composed of triple helix strands of polypeptides. The polypeptides are held together by hydrogen bonds between the polypeptide strands. On heating the collagen reforms so that the overall length is decreased. This thermal modification phenomenon is called corneal shrinkage. One object of the reshaping procedure is to allow for ocular changes in the stroma without inducing clinically significant damage to the viability of the other layers. Although some damage is inherent in this method, clinically insignificant damage means that the eye continues to function optically and that the cellular layers continue to live and regenerate.

Heating the collagen of the stroma to a temperature of at least 55° to 58° C. and up to a maximum of about 65° C. causes the collagen to shrink thereby changing the shape of the cornea 50. This heating process can be effectuated by directing light energy 70 onto the cornea 50 to cause absorption of energy to heat the stromal collagen to the desired temperature. This is done by providing a light source that radiates light energy that is characteristically deposited within a specified depth of the corneal tissue. Light energy 70 as used in this application is not limited to the visible spectrum. The selection and control of the source of light energy 70 that induces the thermal changes to the cornea is critical. The variables used to select the appropriate amount and type of light energy 70 are wavelength, irradiance level, and time (duration). It is essential that these three variables be selected so that the amount of light is functionally effective to produce a predetermined change in the anterior portion only of the stroma. The light source can be either a laser or a non-laser light source providing it emits radiation of the appropriate wavelengths to be absorbed within the stroma without penetrating deeply into the eye in a manner that can damage the endothelium of the cornea or other structures of the eye. The light energy 70 must also be of a type that can be directed onto the cornea and controlled to produce the appropriate thermal changes.

This detailed description of the invention relates to the use of a hydrogen fluoride chemical laser. Use of this particular example does not limit the light energy source, duration of exposure, intensity, preferred wavelength, or laser to the hydrogen fluoride chemical laser. For example, thulium based lasers (also referred to as thulium based lasers), i.e.,a Tm:YAG, Tm:YSGG, or Tm:YLF laser, producing light with a wavelength of 1.90 to 2.02 microns can be effectively used with this invention. The detailed description is not intended to be limiting on this invention but is merely illustrative of a preferred embodiment.

It should be understood that the term wavelength includes wavelengths of slightly greater and slightly smaller size and is often described for purposes of this application as "one or more wavelengths." It has been found that the optimum wavelength range is about 2.4 microns to about 2.67 microns, with the most preferred wavelengths being approximately 2.5 to 2.6 microns. Light within this range of wavelengths is absorbed primarily in the anterior of the stroma. Light having wavelengths of 1.90 to 2.02 and 3.8 to 7.0 microns may also be utilized in this invention. In general, light having wavelengths that are absorbed within a penetration depth of 50 to 200 microns within the cornea are usable. Since human corneas are typically 500 microns or more in thickness the initial absorption of light energy at these wavelengths does not heat the corneal endothelium significantly thus preventing damage to this vulnerable structure. By controlling the duration and irradiance level of light emitted at these wavelengths, substantial thermal conduction of the absorbed light energy can be prevented so that the conducted heat does not damage the corneal endothelium.

A preferred light source is a hydrogen fluoride light source. The most preferred light source is a hydrogen fluoride chemical laser that is tuned to produce only those wavelengths of hydrogen fluoride chemical laser radiation that are characteristically absorbed in the first 50 to 200 microns of the anterior region of the cornea. The wavelengths characteristically emitted by a hydrogen fluoride chemical laser system fall within the range of about 2.4 microns to about 3.1 microns. The wavelengths chosen for use with this invention fall within the range of approximately 2.4 microns to about 2.67 microns with the most preferred wavelengths being 2.5 to 2.6 microns. An example of one light source that can be utilized with the current invention is a modified Helios hydrogen fluoride mini-laser (Helios Inc., Longmont, Colo.). This modified laser system uses special resonator optics that are designed to allow laser action on certain hydrogen fluoride wavelengths while suppressing all other wavelengths.

The light energy source is combined with a means for directing and controlling the light beam from the light source accurately onto corneal surfaces. This will generally include an optical delivery system consisting of beam directing or focusing optics together with an optical shutter. The optical delivery system allows control of the delivery parameters such as geometry and dose to produce the desired predetermined reshaping of the cornea. It also allows the control of the irradiance level and duration of the light energy directed upon the eye necessary to beat the collagen in the cornea to the point where it will shrink but not be destroyed and to prevent conduction of the thermal energy that could damage the endothelium.

The preferred duration of exposure of the cornea to or time for application of the light energy is less than about 1 second. Most preferably the time exposure is from about 10 milliseconds to about 100 milliseconds, with the most preferred duration being approximately 10 to 50 milliseconds. The light energy is actually applied in an intermittent or pulse form with each pulse being less than 1 second. The level of irradiance is typically selected to be a level wherein absorption is substantially linear. In the most preferred embodiments of this invention, the irradiance level is less than $1 \times 10^8$ W/cm$^2$. The variables of wavelength, duration and irradiance are highly interdependent. These variables must be interrelated in a way that a functional amount of light is delivered to the cornea to make the desired predetermined physical changes in the curvature of the cornea without eliciting a wound healing response. A preferred interrelationship of variables includes wavelengths of 2.4 to 2.67 microns, a duration of less than 1 second and an irradiance level of less than $1 \times 10^8$ W/cm$^2$.

Various geometric patterns and temporal periods of radiation produce corrections of different types and magnitude of ocular refractive errors. Referring now to FIG. 8, various geometric patterns and spatial orientations of treatment zones are shown that provide the desired corrective effect. These patterns are typically provided on one or more surfaces of the masking means 40 of this invention. Tangential lines, radial lines, annular rings, and combinations have been shown to be useful in obtaining corrective measures with this invention. In all cues the procedure results in patterns of shrinkage. The preferred method used with this invention does not impact the central optic zone of the cornea. Generally all light energy applications are to the outer region of the cornea. Such an application regimen substantially limits risk to patients since the critical central optic zone is not actually treated. In a particularly preferred embodiment the light energy is applied as a geometric predetermined pattern of spots, both symmetric and axisymmetric.

It is critical that at no time during or after application of the functionally effective dose of light energy is a substantial wound-heal response initiated in the cornea and specifically, in the stromal tissue of the cornea. In this connection, a substantial wound-healing response is one that causes stromal collagen sythesis and regrowth that produces a change in curvature of the anterior surface of the cornea. Any substantial wound-healing response is incompatible with the clinically insignificant damage that is the objective of the procedure, The corneal wound-healing response in man is complex and not perfectly understood [R. W. Beuerman, C. E. Crosson, and H. E. Kaufman (editors), *Healing Processes in the Cornea* (Gulf Publishing Co., Houston, Tex., 1989)].

Following a substantial wound to the stromal tissue, a sequence of processes occurs that result in the synthesis of new collagen that is initially present in the form of disorganized fibers of nonuniform diameters and Irregular orientations. These new collagen fibers degrade corneal transparency since they scatter light. Over a period of several months, the new collagen fibers may be transformed, at least in part, into new stromal lamellae that have more organized structures that transit light properly without scattering. As these new stromal lamellae are formed, the dimensions and mechanical properties of the stromal tissue change, thereby causing changes in anterior corneal shape. A substantial wound-healing response is avoided by careful control of the nature and extent of stromal collagen alternation. Therefore, the results of the corneal reshaping produced by application of a functionally effective dose of light are predictable and controllable and are not subject to long-term modification due to a substantial wound-healing response. Alternate procedures such as excimer laser photorefractive keratectomy suffer from instability of refractive correction due to long-term stromal regrowth and corneal reshaping (i.e.. they produce clinically significant damage).

Used with the coupler, the output beam of radiation from a hydrogen fluoride chemical laser is directed by a series of beam steering mirrors onto an X-Y scanner. The scanner is driven by computer controlled electronics to produce a swept beam that is directed onto a focusing lens that produces a specified beam diameter on the front surface of the cornea. The focused beam is slewed over the front surface of the cornea with a specified slew rate and geometric pattern. A computer controlled optical shutter is used to control the temporal duration of application of the slewed beam which may be continuous or interrupted during laser irradiation of the cornea. Many variations and combinations of optical delivery systems are available and are known to those skilled in the art. Any optical delivery system which will provide the precision necessary to practice the current method will suffice.

A means to measure the curvature of the cornea before, during and after the cornea reshaping process is utilized. Any keratometric device, such as a video keratometer, can be used to produce accurate corneal topographic maps of the cornea. The corneal topographic maps, together with refractive measurements of the eye, are used to establish the geometry and dose of light energy required to produce correction of ocular refractive errors. After the application of light energy, keratometric measurements are performed to produce corneal topographic maps that verify that the desired correction has been obtained. Keratometric measurements may also be made during the cornea reshaping process as multiple applications of light energy may be needed to reach the correct "end point" (an emmetropic eye). Examples of keratometers which may be used include the Canon SK-1 surgical keratometer and the PKS-1000 photokeratoscope (Sun Contact Lens Co. Ltd., Palo Alto, Calif.). A preferred keratometer will provide digitized output from which a visual display is producible to show the cross-sectional profile of the anterior surface curvature of the cornea.

During thermal processing at the collagen shrinkage temperature, collagen shrinks along the main fiber axis direction to a new length that is determined in part by the tension acting along the fiber direction [J. C. Allain et al., *Connective Tissue Research*, 7, 127–133 (1980)]. Collagen swells transverse to the main fiber axis direction. At elevated temperature (i.e., at the corneal shrinkage temperature), collagen is much less rigid due to the loss of weak bonds (termed hydrogen bonds) that hold collagen molecules in a precise structural pattern (a triple helix) at physiological temperature. Hence, at the collagen shrinkage temperature, stromal collagen is much more plastic and is capable of being molded into a new shape. Once formed into a new shape at the collagen shrinkage temperature, the stromal collagen may then be cooled to physiological temperature. At physiological temperature, new hydrogen bonds form and these tend to preserve the stromal collagen in its new shape.

FIG. 7 is a graphic representation of temperature in the various layers of the cornea using a hydrogen fluoride laser. The graph shows the effectiveness of using a heat sink or coupler. With the extra control provided by the coupler, light energy of a higher irradiance level with a longer exposure time resulted in harmless temperatures in the epithelium and Bowman's layer while allowing functionally effective temperatures within the anterior part of the stroma.

Typical depths of microstructural layers of the cornea are indicated for the epithelium (Ep), the Bowman's layer (B), the stroma, Descemet's membrane (D), and the endothelium (En). The calculations use estimated thermal properties (thermal conductivity, thermal diffusity, and heat capacity) for human corneas together with the optical absorptions coefficient laser wavelengths produced by a hydrogen fluoride (HF) chemical laser. The temperature distributions that peaks on the anterior surface (Z=0) of the cornea is for application of a hydrogen fluoride chemical laser source (at a predetermined wavelength of approximately $\lambda$=2.61 $\mu$m) at a fixed irradiance of 30 W/cm$^2$ and a fixed time of 80 ms. The temperature distribution that peaks within the anterior portion of the stroma (labeled "with coupler") is calculated for the same laser wavelength but includes the effects of the coupler in thermal contact with the anterior surface of the cornea. In this case, the HF chemical laser source is applied for a fixed irradiance of 100 W/cm$^2$ and a fixed time of 100 ms. The desired temperature range (approximately 55° C. to 65° C.) for collagen shrinkage without gross thermal damage is shown within the corneal stroma.

A typical apparatus for performing the reshaping procedure in conjunction with the coupler invention is described below. The light source, a hydrogen fluoride chemical laser, is installed either in the patient treatment room or in a remote location. The light energy beam either is propagated through an optical path in air or is coupled into a fiber optic cable. The propagated or coupled beam is then directed onto beam steering, scanning, and focussing optics. An optical shutter is also incorporated within the beam train to provide the correct exposure duration. The beam delivery system includes the scanning system that controls the movement of the laser beam on the predetermined and preselected portion of the patient's cornea. Additionally, the shutter and scanning system are computer controlled to synchronize their actions and to obtain accurate delivery of the functionally effective light beam onto the patient's cornea.

The final delivery optics of the optical delivery system are mounted securely on the patient treatment table. These optics have XYZ coordinate translation adjustments and $\Theta\Phi$ angular adjustments to permit the beam to be aligned and positioned accurately with respect to the eye that is to be treated. A beamsplitter is used to sample a small portion (typically, a few percent) of the final output beam that is to be directed onto the patient's eye. This small portion of the beam is directed to beam diagnostic instrumentation to measure laser beam parameters such as power, spot size, and irradiance distribution. (As one alternative, a tracer beam mounted in coaxial alignment may be used to verify alignment.)

The patient lies down on a table that includes a head mount for accurate positioning and an eye restraining device that contains the coupler to provide protection to the anterior surface structures of the cornea, shape the cornea by action of a template surface, mask the surface regions of the cornea that are not to be treated, and thermostatically controlling the initial corneal temperature. The coupler is attached to an articulated arm holding the coupler in place. The arm is attached to a stable platform, thereby restraining the eye in place. The patient is looking up during the procedure and the light beam is directed vertically downward onto the eye of the patient that is to be treated.

The physician who performs the treatment uses an ophthalmic surgical microscope, together with a visible tracer laser beam (from a low energy visible laser such as a helium-neon laser) that is collinear with the treatment beam, in order to verify the proper positioning of the treatment beam. The physician also uses a keratometer such as a separate video keratometer or a surgical keratometer that mounts in-line with the ophthalmic surgical microscope in order to measure corneal curvature. Further, the physician sets computer controlled electronics to control the optical delivery system so as to produce the correct pattern, dose, and exposure duration of the beam.

The coupler 10 is illustrated along with the other apparatus used in the procedure schematically by the flow chart in FIG. 6. This flow chart is intended to show a control means utilized by the physician as the focal point for controlling all variables and light emission devices. The control means is connected to the laser system, the beam delivery system, the scanning system and the keratometer. A light source (in the figure, a laser system) is used to produce functionally effective light. The beam of light is delivered and scanned to produce the correct pattern and dose of functionally effective light on the anterior surface of the cornea. A coupling means is used to provide a heat sink for protection of the anterior surface of the cornea, a template for reshaping the anterior surface of the cornea, a thermostat for accurate and reproducible temperature control prior to laser treatment, a mask for protection of regions of the anterior surface of the cornea that are not intended to be treated, and a positioner/restrainer for accurate positioning of the light source beam on the anterior surface of the cornea and for restriction of eye movement during the treatment. A keratometer is used to perform corneal topography measurements before, during, and after the procedure.

A control means is used to provide predetermined values of pattern and dose of the laser beam on the anterior surface of the cornea. It is suggested that the control means have all the controls necessary for the surgeon to have complete control of the operation including suitable displays of the operation variables showing what has been preselected and what is actually delivered. For example, the pattern of the laser beam should be preselected and be capable of being varied by the surgeon. The pulse duration, the number of pulses to be delivered, the number of pulses actually delivered to a particular location on the eye and the power of each pulse should also be controlled. The control means may be a suitable computer with a terminal at the surgeon's location allowing display of all elements of the operation which may be of interest to the surgeon.

It is essential to understand that one of the primary advantages enjoyed by the practice of this invention is the noninvasive nature of the application process and the fact that no substantial wound-healing response is produced in the cornea. Although the changes to the corneal shape and curvature are long-term physical changes, there are controls in place that prevent the likelihood of there being any risk whatsoever to the patient. Typically the central optic zone, the only zone critical to eye sight, is untouched by light energy. It is important to note that the viability of the corneal endothelium, a delicate and critical layer to human eye sight, together with other essential visual components of the eye are maintained throughout the procedure.

Although the preferred embodiment of the apparatus of this invention has been described hereinabove in some detail, it should be appreciated that a variety of embodiments will be readily apparent to those skilled in the art. The description of the apparatus of this invention is not intended to be limiting on this invention but is merely illustrative of the preferred embodiments of this invention. Other apparatus and components and variations which incorporate modifications or changes to that which have been described herein are equally included within this application.

What is claimed is:

1. A method of reshaping an outside surface of a cornea of an eye, comprising:

engaging an outside surface of the eye surrounding the cornea with a coupler structure that also contacts the outside surface of the cornea with a concave surface having a shape corresponding approximately to a desired emmetropic shape of the corneal outside surface, the concave surface being transparent to infrared radiation, providing a liquid layer between the outside surface of the cornea and the concave surface of the coupler, passing infrared radiation through the concave surface of the coupler, liquid layer and into the cornea in order to raise the temperature of collagen tissue within the cornea sufficiently to shrink said tissue without damaging an endothelium layer of the cornea, and urging the concave surface of the coupler against the outside surface of the cornea during the passing of infrared radiation.

2. The method according to claim 1 wherein the engaging of the outside surface of the eye surrounding the cornea includes attaching the coupler structure to the outside of the eye surrounding the cornea.

3. The method according to claim 2 wherein the urging of the concave surface of the coupler against the outside surface of the cornea includes engaging the outside surface of the eye surrounding the cornea with the coupler by creating a vacuum between the coupler and the outside surface of the eye surrounding the cornea.

4. The method according to any one of claims 1–3, additionally comprising removing heat from the outside surface of the cornea through the concave surface of the coupler while said infrared radiation is being passed therethrough.

5. The method according to any one of claims 1–3 wherein the providing of a liquid layer includes providing a liquid layer of an ophthalmic solution.

6. The method according to any one of claims 1–3, additionally comprising positioning on the coupler in a region of the concave surface thereof a mask to block said infrared radiation from reaching a central optic zone of the cornea while allowing said infrared radiation to enter the cornea in an area surrounding said central optic zone.

7. The method according to any one of claims 1–3, additionally comprising:

removing heat from the outside surface of the cornea through the concave surface of the coupler while said infrared radiation is being passed therethrough, and positioning on the coupler in a region of the concave surface thereof a mask to block said infrared radiation from reaching a central optic zone of the cornea while allowing said infrared radiation to enter the cornea in an area surrounding said central optic zone.

8. The method according to claim 7 wherein the providing of a liquid layer includes providing a liquid layer of an ophthalmic solution.

9. The method according to claim 1 wherein the passing of infrared radiation point the cornea includes selecting said radiation to lie within a range of from 1.90 to 2.02 microns.

10. The method according to claim 1 wherein the passing of infrared radiation into the cornea includes selecting said radiation to lie within a range of from 2.4 to 2.67 microns.

11. The method according to any one of claims 1–3 wherein the passing of infrared radiation into the cornea includes positioning a source of said infrared radiation remote from the eye and conducting said infrared radiation to the cornea through a fiber optic cable and said coupler.

12. The method according to claim 7 wherein the passing of infrared radiation into the cornea includes positioning a source of said infrared radiation remote from the eye and conducting said infrared radiation to the cornea through a fiber optic cable and said coupler.

13. The method according to any one of claims 1–3 wherein the passing of infrared radiation into the cornea includes scanning a beam of said infrared radiation across said coupler and through said concave surface.

14. The method according to any one of claims 1–3, additionally comprising positioning on the coupler in a region of the concave surface thereof a mask to block said infrared radiation from reaching a central optic zone of the cornea while allowing said infrared radiation to enter the cornea in an area surrounding said central optic zone, and wherein the passing of infrared radiation into the cornea includes scanning a beam of said infrared radiation across said coupler in the area surrounding said mask and through said concave surface.

15. A method of reshaping an outside surface of a cornea of an eye, comprising:

engaging an outside surface of the eye surrounding the cornea with a coupler structure that also contacts the outside surface of the cornea with a concave surface having a shape corresponding approximately to a desired emmetropic shape of the corneal outside surface, the concave surface being transparent to infrared radiation, providing a mask on the coupler over a portion of the concave surface, passing infrared radiation through the concave surface of the coupler around the mask and into the cornea in order to raise the temperature of collagen tissue within the cornea sufficiently shrink said tissue without damaging an endothelium layer of the cornea, urging the concave surface of the coupler against the outside surface of the cornea during the passing of infrared radiation, and removing heat from the outside surface of the cornea through the concave surface of the coupler while said infrared radiation is being passed therethrough.

16. The method according to claim 15 wherein the passing of infrared radiation into the cornea includes scanning a beam of said infrared radiation across said coupler.

17. The method according to claim 15 wherein the passing of infrared radiation into the cornea includes positioning a source of said infrared radiation remote from the eye and conducting said infrared radiation to the cornea through a fiber optic cable and said coupler.

* * * * *